US006773695B2

(12) United States Patent
Kündig et al.

(10) Patent No.: US 6,773,695 B2
(45) Date of Patent: Aug. 10, 2004

(54) MODULATION OF ALLERGIC RESPONSE

(75) Inventors: Thomas M. Kündig, Zurich (CH); Stephen J. McCormack, Claremont, CA (US)

(73) Assignee: MannKind Corporation, Valencia, CA (US)

( * ) Notice: Subject to any disclaimer, the term of this patent is extended or adjusted under 35 U.S.C. 154(b) by 0 days.

(21) Appl. No.: 09/804,464

(22) Filed: Mar. 13, 2001

(65) Prior Publication Data

US 2002/0061315 A1 May 23, 2002

Related U.S. Application Data

(60) Provisional application No. 60/237,724, filed on Oct. 5, 2000.

(51) Int. Cl.$^7$ ........................ A61K 49/22; A61K 39/35; A61K 39/36; A61K 35/64
(52) U.S. Cl. .................. 424/9.4; 424/184.1; 424/275.1; 424/539; 424/810
(58) Field of Search .............................. 424/184.1, 810, 424/275.1, 539, 9.4

(56) References Cited

U.S. PATENT DOCUMENTS

| 3,849,551 A | 11/1974 | D'Antonio |
| 5,593,877 A | 1/1997 | King |
| 5,612,209 A | 3/1997 | King |
| 5,804,201 A | 9/1998 | King |

FOREIGN PATENT DOCUMENTS

| WO | PCT WO 99/02183 | 1/1999 |
| WO | WO 00/50044 A1 | 8/2000 |
| WO | WO 01/82963 A2 | 11/2001 |

OTHER PUBLICATIONS

Hong et al, J Immunological Methods 120: 151–7.*
Hellman et al, Handbook of Experimental Pharmacology 133(vaccines): 499–526, 1999.*
Coupey et al, Cytokine 5(6): 564–9, Nov. 1993.*
Zinkernagel et al, Immunol Rev 156: 199–209, Apr. 1997.*
Banks et al, Chemistry and Pharmcology of Honey–bee venom In: Piek T, ed. Venoms of the Hyemoptera. London: Academic Press; 1986, pp. 329–416.*
Guidry et al, J Dairy Science 77(10): 2965–74, 1994.*
Hellman L. et al., Allergy Vaccines. A Review of Developments: Clinical Immunotherapeutics, ADIS International, Aug. 1996, pp. 130–142, vol. 6, No. 2, Auckland, NZ.
Lambert, Laura A. et al: "Intranodal Immunization with tumor lysate–pulsed dendritic cells enhances protective anti–tumor immunity.", Cancer Research, Jan. 15, 2001, pp. 641–646, vol. 61, No. 2.
L. Parijs, et al., "Homeostasis and Self–Tolerance in the Immune System: Turning Lymphocytes off", Science, vol. 280, Apr. 10, 1998, pp. 243–248.

R. Tepper, et al., "IL–4 Induces Allergic–like Inflammatory Disease and Alters T Cell Development in Transgenic Mice", Cell, vol. 62, Aug. 10, 1990, pp. 457–467.

P. Mark, et al., "Human T and B cell immune responses to Fel d 1 in cat–allergic and non–cat–allergic subjects", Clinical and Experimental Allergy, vol. 26, 1996, pp. 1316–1328.

A. Helbling, et al., "Allergy to honey: relation to pollen and honey bee allergy", Allergy, vol. 47, Feb. 1992, pp. 41–49.

M. dos Reis, et al., "Acute Renal Failure in Experimental Envenomation with Africanized Bee Venom", Renal Failure, vol. 20, 1998, pp. 39–51.

A Dirksen, et al., "Common Components in Pollen Extracts", Allergy, vol. 35, 1980, pp. 611–616.

H. de Groot, et al., "Allergy to bumblebee venom I. Occupational anaphylaxis to bumblebee venom: diagnosis and treatment", Allergy, vol. 50, 1995, pp. 581–584.

T. Lehner, et al., "Induction of Mucosal and Systemic Immunity to a Recombinant Simian Immunodeficiency Viral Protein", Science, vol. 258, Nov. 20, 1992, pp. 1365–1369.

T. Lehner., et al., "Mucosal Model of Genital Immunization in Male Rhesus Macaques with a Recombinant Simian Immunodeficiency Virus p27 Antigen", Journal of Virology, vol. 68, Mar. 1994, pp. 1624–1632.

T. Lehner, et al., "Targeted Lymph Node Immunization with Simian Immunodeficiency Virus p27 Antigen to Elicit Genital, Rectal, and Urinary Immune Responses in Nonhuman Primates", Journal of Immunology, Aug. 15, 1994, vol. 153(4)pp. 1858–1868.

B. Wallner, et al., "Peptide Therapy for Treatment of Allergic Disease", Clinical Immunology and Immunopathology, vol. 80, No. 2, Aug. 1996, pp. 105–109.

R. Valenta, et al., "The immunoglobulin E–allergen interaction: a target for therapy of type I allergic diseases", Int. Arch Allergy Immunology 1998, 116: pp. 167–176.

H. Malling, "Allergen–specific immunotherapy. Present state and directions for the future", Allergy 1999, 54, pp. 30–33.

C. Akdis, et al., "Immunologic mechanisms of specific immunotherapy", Allergy 1999, 54, 31–32.

(List continued on next page.)

*Primary Examiner*—Christina Chan
*Assistant Examiner*—Phuong Huynh
(74) *Attorney, Agent, or Firm*—Banner & Witcoff, Ltd.

(57) ABSTRACT

The modulation or elimination of an allergic condition according to the invention can be achieved by injecting small amounts of allergen directly into a lymph node, which greatly reduces the potential for side effects.

16 Claims, 8 Drawing Sheets

OTHER PUBLICATIONS

E. Raz, et al., "Deviation of the Allergic IgE to an IgG Response by Gene Immunotherapy", Intern. Rev. Immunol., vol. 18, pp. 271–289, 1999.

D. Lee, et al., "Inhibition of IgE Antibody Formation by Plasmid DBA Immunization is Mediated by both CD4+ and CD8+ TCells", Int. Arch Alergy Immunol 1997; 113: 227–230.

J. McGhee, et al., "Mucosal Th1–versus Th2–Type Responses for Antibody–or Cell–Mediated Immunity to Simian Immunodeficiency Virus in Rhesus Macaques", Journal of Infectious Diseases 1999; 179: pp. S480–S484.

T. Lehner, et al., "Up–regulation of beta–chemokines and down–modulation of CCR5 receptors inhibit simian immunodeficiency virus transmission human primates" Immunology 2000; 99: pp. 569–577.

S. Shinall, et al., "Identification of Murine Geminal Center B Cell Subsets Defined Expression of Surface Isotypes and Differentiation Antigens", Journal of Immunology Jun. 1, 2000, vol. 164(11), pp. 5729–5738.

H. Kitagaki, et al., "Distinct In Vivo and In Vitro Cytokine Profiles of Draining Lymph Node Cells in Acute and Chronic Phases of Contact Hypersensitivity: Importance of a Type 2 Cytokine–Rich Cutaneous Milieu for the Developemnt of an Early–Type Response in the Chronic Phases", Journal of Immunology, 1999, 163: 1265–1273.

A. Aubertin, et al., "Generation of CD8+ T Cell–Generation Suppressor Factor and β–Chemokines by Targeted Iliac Lymph Node Immunization in Rhesus Monkeys Challenged with SHIV–89.6P by the Rectal Route", Aids Research and Human Retroviruses 2000, vol. 16, pp. 381–392.

* cited by examiner

MODULATION OF ALLERGIC RESPONSE

This application incorporates by reference copending provisional application Serial No. 60/237,724 filed on Oct. 5, 2000.

TECHNICAL FIELD OF THE INVENTION

This invention relates to the field of allergy vaccines and treatments. More particularly, the invention contemplates a method of delivery of allergens.

BACKGROUND

An allergy is the result of a powerful immune system reaction against a substance that should normally be inoffensive to the host. A recent survey by the American College of Allergy, Asthma and Immunology (ACAAI) reveals that approximately 38% of the US population suffers from allergies (*Immunotherapy Weekly*, Nov. 29, 1999). If the ACAAI estimate is correct, at least 85 million Americans have allergies.

Allergies are caused by an imbalance or hypersensitivity of the immune system, leading to a misdirected immune response. An allergic response occurs when the immune system reacts inappropriately to highly specific agents that in most people do not cause an immune response, such as tree and grass pollens, cockroaches, dust mites, animal dander, latex, or honeybee, wasp and fire ant venoms. Other common allergens include foods such as peanuts, tree nuts, milk, fish, shellfish, eggs, soy, wheat, honey, cantaloupe, strawberries and tropical fruits, drugs such as penicillin, anesthetics, serum, some viruses, bacteria and protozoa, and mold. Delayed type hypersensitivity reactions may occur in response to urushiol, an oil found in poison ivy, poison oak and sumac, resulting in a severe itchy rash and formation of oozing blisters.

Allergens are discussed inter alia in the following articles which are incorporated herein by reference: Blaauw P J, Smithuis O L, Elbers A R. The value of an in-hospital insect sting challenge as a criterion for application or omission of venom immunotherapy. *J Allergy Clin Immunol.* 1996;98:39–47; Bousquet, J, Lockey, R F, Malling, H-J. Allergen immunotherapy: therapeutic vaccines for allergic diseases [WHO Position Paper]. *World Health Organization, Allergy.* 1998; 53(suppl):12–16; Lack G, Nelson H S, Amran D, et al. Rush immunotherapy results in allergen-specific alterations in lymphocyte function and interferon-γ production in CD4+ T cells. *J Allergy Clin Immunol.* 1997;99:530–538; Müller U. Diagnosis and treatment of insect sting sensitivity. *J Asthma Res.* 1966;3:331–333; Weber, R W. Immunotherapy with allergens. *JAMA.* 1997;278:1881–1887.

The first exposure to an effective allergen causes only a mild immune response that sensitizes the immune system to the substance. However, subsequent exposures to the allergen result in allergic symptoms, typically in a dose dependent manner (ie, the allergen must reach a certain threshold), and may cause an increasingly severe response with repeated exposures. Allergic symptoms include itching and swelling of affected tissues, rashes, muscle spasms and other more severe symptoms. See Table 1 below for the Müller classification of allergic reactions. The type of symptom depends on the specific allergen, the part of the body where exposure occurs, and the degree of sensitization of the individual. Allergens that are inhaled often cause nasal congestion, itchy nose and throat, and mucus production. In highly allergic individuals or with higher doses of allergen, coughing, wheezing, or similar symptoms occur. In contrast, ingested allergens cause itching of the throat, vomiting, stomach cramps, diarrhea, and skin rashes or shock, in cases of strong sensitivity. Eczema is also associated with allergies; a decrease in allergies results in an improvement of eczema.

TABLE 1

Müller Classification of Allergic Reactions

| | |
|---|---|
| Large local reactions | Swelling at site of sting with diameter >10 cm, lasting >24 h |
| Systemic reactions | |
| Grade I: | Generalized urticaria, itching, malaise, anxiety |
| Grade II: | Any of the above, plus 2 more of the following: angioedema (also grade II if occurs alone), constriction in chest, nausea, vomiting, diarrhea, abdominal pain, dizziness |
| Grade III: | Any of the above, plus 2 or more of the following: dyspnea, wheezing, stridor (any of these alone are grade III), dysphagia, dysarthria, hoarseness, weakness, confusion |
| Grade IV: | Any of the above, plus 2 or more of the following: fall in blood pressure, collapse, loss of consciousness, incontinence (urine, stool), cyanosis |

The largest numbers of allergy sufferers, about 45 million Americans, are those who are allergic to pollen and are afflicted with airway diseases such as allergic rhinitis, hay fever and asthma. People with seasonal pollen allergies often develop cross-sensitivity to other allergens that are present all year, such as dust mites. People with chronic respiratory allergies often develop asthma, which is the consequence of long-term activation of the allergic/inflammatory response in the respiratory system. The symptoms of asthma include coughing, wheezing, and shortness of breath due to a narrowing of the bronchial passages, excess mucus production and inflammation. Asthma can be disabling and sometimes fatal.

Cockroach allergy is an allergy to the excrement of cockroaches, and is a trigger of asthmatic attacks. Dust mite allergy is an allergy to the excrement of a microscopic organism living in dust found in all dwellings and workplaces, and in virtually all bedding. Dust mites are perhaps the most common cause of perennial allergic rhinitis, producing symptoms similar to pollen allergy and asthma. About half of all allergy sufferers are allergic to dust mites.

Over 10 million Americans are allergic to animals. Household pets are the most common source of such reactions. Many people think the fur of cats and dogs provokes pet allergies. However, the major allergens are proteins secreted by oil glands in the animal's skin and shed in dander; and in the saliva, which sticks to the fur when the animal licks itself. When the saliva carrying the proteins dries, the proteins float into the air and are inhaled by people. Some rodents, such as guinea pigs and gerbils, have become increasingly popular as household pets. They, too, can cause allergic reactions in some people, as can mice and rats.

Between 6 and 7 million Americans are affected by food allergies. Food allergies are different from food intolerances, since food intolerances do not involve the immune system. Up to 3 million Americans are highly allergic to peanuts and tree nuts. Eight foods account for 90% of food allergies: milk, fish, peanuts, tree nuts, eggs, soy, wheat, and shellfish. In these cases, systemic reactions may be severe, such as onset of allergic shock. To avoid serious consequences including death, people allergic to foods carry strong antihistamines. Even so, treatment or preventative measures for food allergies are often only marginally effective. The primary therapy is simply total avoidance of the specific allergen. Conventional subcutaneous allergy shots are ineffective against food allergies.

Approximately 5 million people in the Unites States are allergic to bee or wasp stings, in many cases with potentially life threatening symptoms. Three out of 5 of allergic people stung will experience a severe reaction if stung again.

In developed countries, the frequency of allergic reactions has increased dramatically in recent years, to the extent that about 20% or more of the population of the United States has allergies to some common substance. Overall, allergic diseases are the 6th leading cause of chronic disease in the United States. Heredity, environmental conditions, type and number of exposures, and various physiological factors such as stress, fatigue and emotional upset can increase the sensitivity of the immune system and predispose a person to allergies.

The reason for the increase in the number of allergy sufferers is currently under intense scientific debate. There are several possible explanations on which most scientists can agree. Air pollution with nitric oxides ($NO_x$) may play a role in the increasing frequency of allergic airway disease. Not only do nitric oxides increase the production of allergenic proteins in pollen, but they also directly damage sensitive cells lining the airway of the throat and lungs. This damage has the effect of allowing more allergens to get into the body through the damaged cells that normally act as a protective lining. The problem is made worse when smog particles become adsorbed to pollen and act as an adjuvant, enhancing the effects of the allergens.

Scientists widely believe that a phenomenon known as cross-reactivity may also be a cause of the increasing allergy problem. Cross-reactivity occurs when a person, exposed to one particular allergen, subsequently has increased sensitization to another, similar kind of allergen. Food allergies are commonly found to be associated with allergic airway diseases. For example, if the pollen of the hazelnut tree is inhaled, a person may develop an allergy to hazelnuts. Cross-reactivity between allergens from pollen and allergens found in foods may in fact be one of the major causes of food allergies in adults.

In addition, scientists are considering that the large-scale vaccination campaigns and wide spread use of antibiotics over the last few decades, which have dramatically reduced the severity of infectious diseases, may also have altered the population's immune system, making people more susceptible to allergies. While modem medicine and vaccines have lessened the burden of infectious disease, a possible trade-off may be the increased prevalence of allergies.

In light of the escalating social and economic impact of allergies, tackling allergic diseases has become a medical undertaking of growing importance. Doctors use three general approaches to help people with allergies: they advise patients on ways to avoid the allergen as much as possible, prescribe medication to relieve allergic symptoms, and administer a series of allergy shots. Several potent anti-allergy drugs exist today. However, these drugs merely treat the symptoms of allergies, and some of them carry the risk of serious side effects. Another strategy is to develop ways of conditioning the immune system to respond "appropriately" to allergens. Only this last approach, allergy shots or immunotherapy, is a causative treatment for allergies.

Allergen immunotherapy or hyposensitization is the practice of administering gradually increasing quantities of an allergen to an allergic subject to ameliorate the symptoms (allergic reaction) associated with subsequent exposure to the causative allergen. Allergen immunotherapy was introduced in 1911 to treat "pollinosis" and is currently established as the preferred treatment in the case of severe allergies.

Allergy shots have proven useful in many cases to significantly and permanently relieve the extent of suffering experienced by allergic individuals. In fact, the current allergy shot approach is the only method that may be regarded as a curative means to reverse this disease condition. Early desensitization using the allergy shot approach to specific allergens has also proven somewhat effective against the occurrence of cross-reactive allergies to other substances. For example, a patient receiving allergy shots to treat hay fever by desensitizing against pollen has a decreased risk of becoming allergic to cat hair or other common allergens.

Although allergy shots are currently the only means for treating the disease rather than the symptoms, there are obvious disadvantages to this treatment as it is performed today. Conventional immunotherapy is lengthy, lasting from 2 to 5 years, expensive, and only marginally effective. This treatment is ineffective in one-third of all allergy sufferers and only temporarily effective in one-third of allergic individuals. Immunotherapy has long term effectiveness in only the remaining third of the allergic population.

The treatment duration for conventional immunotherapy is long and time consuming, usually comprising a total of 30 to 100 allergen injections, each requiring 1 hour or more of strict medical supervision after the shot is administered. For desensitization to certain allergens which are known to cause severe side effects, such as insect venom cat hair or dust mites, patients must remain in the doctor's office for an hour after each injection for observation. Thus, medical and economic costs are very high for this type of treatment.

Allergy shot regimens typically involve 2 treatment phases. The $1^{st}$ phase employs about 20 allergy shots. During this phase the amount of allergen injected is increased with each dose, starting with minute amounts (as low as 0.01 $\mu$g). Injections of diluted extracts of the allergen are administered on a regular schedule, usually twice a week or weekly at first, in increasing doses until a maintenance dose of about 100 $\mu$g has been reached. This maintenance dose, reached after about 20 weeks, is then injected every 2 to 4 weeks for a period of 3 or more years.

It usually takes several months and may take up to 3 years to reach a maintenance dose. Patients may experience some relief within 6 months; however, if there is no benefit within 18 months, the shots are generally discontinued. After stopping immunotherapy, about one-third of allergy sufferers no longer have any symptoms, one-third have reduced symptoms, and one-third relapse completely.

In addition, during the desensitization phase, as more allergen is administered the injections usually cause moderate and sometimes severe side effects ranging from soreness and local swelling (wheal) or rash (flare) at the injection site to systemic allergic effects such as generalized skin rash or hives (urticaria), asthma, or even allergic shock (anaphylaxis). Other common side effects of immunotherapy include general itching (pruritis), red eyes and low blood pressure. Side effects usually occur within 20 minutes, although some can develop up to 2 hours after the allergy shot is given. Anaphylaxis refers to an allergic reaction characterized by a sharp drop in blood pressure, hives or welts, and breathing difficulties, that occurs immediately, progresses rapidly and is life-threatening. Anaphylaxis is the most severe reaction that can result from standard immunotherapy.

Development of a specific immune response requires that the cells of the immune system encounter an antigen, and that T and B lymphocytes interact with each other and with other antigen presenting cells (APC) to eliminate extracellular pathogens or toxins. When an allergic person first comes into contact with an allergen, the immune system generates large amounts of a type of antibody called immunoglobin E, or IgE. Each IgE antibody binds with high affinity to one particular allergenic substance. In the case of pollen allergy, the antibody is specific for each type of pollen. For example, one type of antibody is produced to react against mugwort pollen, and another against ragweed pollen. Bee venom, which contains the protein $PLA_2$, elicits anti-$PLA_2$ antibodies. During the initial phase of the immune response, low-affinity anti-$PLA_2$-specific IgG1 antibodies are generated. After repeated stings, patients with normal immunity develop high-affinity anti-$PLA_2$-specific IgG4 antibodies, but patients allergic to bee venom develop anti-$PLA_2$-specific IgE antibodies. Immune-stimulating mast cells in tissue, and basophils in blood will bind to the IgE antibody and release powerful inflammatory mediators (cytokines). These cytokines act on tissues in various parts of the body, such as the respiratory system, causing the symptoms of allergy.

Successful immunotherapy is accompanied by a decrease in $PLA_2$-specific IgE, and an increase in $PLA_2$-specific IgG. The precise mechanisms by which allergen immunotherapy achieves clinical improvement in the symptoms of allergic patients is still not completely clear, but it seems as though IgG antibodies may protect against allergic reaction. Immunotherapy is associated with a reduction in allergen-induced IL-4 and IL-5 cytokine secretion, and a simultaneous increase in IFN-γ secretion by allergen-specific T cells.

SUMMARY OF THE INVENTION

It is one object of the present invention to provide an effective method of delivery of allergens.

It is a further object of the invention to provide a method of delivery of allergens which effectively employs a low dosage of allergens.

It is a still further object of the invention to provide a regimen of treatment for allergies which is effective to modulate an allergic condition after only a few injections.

It is an additional object of the invention to provide a mode of treatment with allergens which is characterized by reduced adverse side effects.

This invention contemplates a method of modulating an allergic response of an individual comprising delivery by direct injection of an allergen to a lymph node of said individual whereby the allergic response is modulated. For individuals who lack lymph nodes or who possess defective lymph nodes, the allergen may be delivered to the lymphatic tissue or to an immune cell. In one specific aspect of the invention the allergen is delivered in combination with an adjuvant, or is precipitated on, or bound to a delivery or formulation substance. Still other aspects of the invention are described in the Description of the Preferred Embodiments of the Invention.

This invention contemplates using intranodal delivery of allergens to re-equilibrate the immune system more effectively than can be accomplished utilizing conventional immunotherapy. The invention provides efficient and effective modulation of a wide variety of allergic responses and represents a major improvement over the current approach. For example, using the preferred embodiments, modulation or elimination of an allergic condition can be achieved with as few as 1 to 3 injections. The targeted delivery also allows the use of smaller amounts of allergen than are used in conventional allergy shots, greatly reducing the potential for side effects such as urticaria, dyspnea, syncope, hypotension, myocardial events and even death.

BRIEF DESCRIPTION OF THE DRAWINGS

FIG. 5 shows ELISA results demonstrating effects on IgG2a titers over time after injection of phospholipase-$A_2$ ($PLA_2$) by different routes of delivery in CBA/J mice.

FIG. 5A, 0.1 μg $PLA_2$ injected intraperitoneally;

FIG. 5B, 10 μg of $PLA_2$ injected intraperitoneally;

FIG. 5C, 0.1 μg $PLA_2$ injected into a lymph node;

FIG. 5D, 10 μg $PLA_2$ injected into a lymph node;

FIG. 5E, 0.1 μg $PLA_2$ injected subcutaneously;

FIG. 5F, 10 μg $PLA_2$ injected subcutaneously.

FIG. 6 shows ELISA results demonstrating effects on IgE titers over time after injection of phospholipase-$A_2$ ($PLA_2$) by different routes of delivery in CBA/J mice.

FIG. 6A, 0.1 μg $PLA_2$ injected intraperitoneally;

FIG. 6B, 10 μg of $PLA_2$ injected intraperitoneally;

FIG. 6C, 0.1 μg $PLA_2$ injected into a lymph node;

FIG. 6D, 10 μg $PLA_2$ injected into a lymph node;

FIG. 6E, 0.1 μg $PLA_2$ injected subcutaneously;

FIG. 6F, 10 μg $PLA_2$ injected subcutaneously.

FIG. 7 shows the relative amounts of IgG2a measured in mice injected intranodally and subcutaneously with $PLA_2$.

FIG. 8 shows the relative amounts of IgE measured in mice injected intranodally and subcutaneously with $PLA_2$.

DETAILED DESCRIPTION

The present invention is useful in any animal having an immune system that includes a lymphatic system. Such field of use generally includes mammals and humans. While the primary use of the invention is likely to be in the treatment of humans, it will also be suitable for treatment of animals, including household pets such as dogs and cats.

The present invention involves the delivery of an allergen by injection directly into a lymph node in order to modulate an allergic response of an individual (for example, to elicit an IgG response) more efficiently than is possible by subcutaneous injection. According to the invention, modulation of an allergic response includes, but is not limited to, diminution or elimination of responses such as alterations in specific IgG levels, alterations in IgG ratios, alterations in specific IgE levels, lowered sensitivity to the allergen or to a cross-reactive allergenic agent, alterations in activated basophils (such as the reduction of the amount of surface IgE), alterations in cytokine profiles (such as increase in type 1 cytokines e.g., IL-2 and IFN γ, vs. type 2 cytokines e.g., IL-4, IL-5), alterations in Radio-Allergosorbent Test (RAST) results, or skin tests, as well as diminution or elimination of symptoms of an allergic response, such as urticaria, itching, malaise, anxiety, angioedema, constriction of the chest, nausea, vomiting, diarrhea, abdominal pain, dizziness, dyspnea, wheezing, stridor, dysphagia, dysarthria, hoarseness, weakness, confusion, fall in blood pressure, collapse, loss of consciousness, incontinence, cyanosis, mucus production, coughing, shock, stomach cramps, rhinitis, hay fever, asthma, inflammation, and the like.

Intranodal administration of allergens has a number of advantages. Because lower doses of allergen can induce an IgG response more potently when injected directly into a lymph node, there are fewer side effects than observed using the conventional allergy shot regime. Moreover, delivery of the allergen to the lymph node by injection is no more painful to the patient than regular subcutaneous injections. An additional advantage of this method is that only two or three treatments typically are necessary to desensitize an individual against an allergen. This lowers the risk of side effects or reaction to the administration, and results in a significant cost savings compared with traditional allergy treatments.

An "allergen" according to the invention can be any substance or portion thereof that elicits an allergic response. For example, common allergens include bee venom, wasp venom, fire ant venom, pollens, including grass, tree and herb pollens, penicillin and other drugs, anesthetics, serum, animals, animal dander, cockroaches, dust mites, food allergens such as those found in peanuts, tree nuts, milk, fish, shellfish, eggs, soy, wheat, honey, fruits, viruses, bacteria, mold, protozoa, or latex. Allergens also can be any component of the allergen that elicits an allergic response, such as $PLA_2$ in bee venom or urushiol in poison ivy. Likewise, an allergen can be a mixture of substances or a crude or purified extract of a generally allergenic composition. These allergens can be recovered from a natural source or can be a synthetic or non-naturally occurring substance, such as a recombinant protein, a synthesized peptide, or a mimetic chemical (including a peptide) that elicits an allergic response similar to a naturally occurring allergen.

A composition useful in the practice of the invention comprises one or more allergens or one or more nucleic acid constructs encoding the allergen(s). The nucleic acid construct can be, for example, RNA or DNA or can simply be a naked nucleic acid construct, such as a plasmid or a virus, encoding the allergen. The allergen or nucleic acid construct can, if desired, be delivered to a specific cell type within a lymph node, such as a dendritic cell. A specific cell type can, if desired, be transfected with the nucleic acid construct so that it expresses the allergen. Optionally, the nucleic acid construct can be targeted via a vector to the desired cell type.

Embodiments of the invention can be adapted to address any disease that includes an allergic-type response. For example, a number of newly discovered and/or little understood viral, bacterial, protozoal, and other diseases exist in the human population. To the extent that such diseases have a pathogenic component that involves an allergic response or an IgE response, embodiments of the invention can be used to reduce the virulence of these diseases and/or to protect people against these diseases. The novel delivery method contemplated by this invention can also be used to alleviate the aspects of asthma and anaphylactic shock associated with hypersensitivity to allergens.

The allergen may be encapsulated in a polymeric material to achieve sustained or pulsatile release. The form of the encapsulation can be, for example, nano- or microspheres, injectable gels, or implants. Suitable polymeric materials include, without limitation, biodegradable PLGA (polylactide-co-glycolide) polyesters, polyanhydrides, polysaccharides (e.g., chitosan, starch, alginate), cellulose derivatives (e.g., ethyl cellulose, hydroxypropylmethyl cellulose), proteins (e.g., collagen, albumin), or polyacrylates.

The allergen is preferably delivered in a physiologically acceptable carrier suitable for injection. In general, any physiologically acceptable carrier known for use with vaccines or allergy shots can be used in the practice of this invention. The choice of such carriers includes, without limitation, water, standard saline solutions, dextrose solutions and albumin water, and is easily within the skill of the art.

In one preferred embodiment, the allergen is delivered in combination with an adjuvant. The adjuvant may be, but is not limited to, one or more of the following: alum, BCG, aluminum hydroxide, aluminum phosphate, calcium phosphate, lipid emulsions, lipid or polymeric nano- or microspheres, micelles, liposomes, saponin, lipid A, or muramyl dipeptide, bacterial products, chemokines, cytokines and hormones, chitosan, starch, alginate, cellulose derivatives (e.g., ethyl cellulose, hydroxypropylmethyl cellulose), nucleic acids, or a nucleic acid construct. One or more of these components may be added to enhance the immune response, increase adsorption of the allergen, provide increased comfort to the patient, and/or slow the release of the allergen to prolong exposure. Alternatively, the allergen may be delivered without an adjuvant or in an aqueous form.

The allergen may be delivered in a dose of about 0.01 μg to about 10 μg or about 0.1 μg to 50 μg and more preferably in a dose from about 0.1 μg to about 10 μg, although the optimal dose may vary depending on the allergen being injected, the weight of the patient, the immune system of the patient, and the like. Effective treatment in many cases may be accomplished with one delivery. In some embodiments, treatment includes from 1 to 15 injections. In preferred embodiments, treatment includes from 1 to 5 injections and more preferably 1 to 3 injections. For example, the standard escalation after a test dose of 0.1 μg involves administration of 1 μg followed by 5 μg and 10 μg. Escalation depends on the patient's tolerance of the previous dose. Multiple injections may be delivered periodically, e.g., over a course of days, once or twice per month, or several times per year.

The dose employed during the initial (desensitization) phase can be from about 0.01 μg to about 10 μg or 0.1 μg to 10 μg delivered in from 1 to 5, preferably from 1 to 3, injections of 1 μg, 5 μg and 10 μg over the course of from several days up to 3 months. In preferred embodiments, the allergen is delivered 2 to 3 times, 1 to 2 weeks apart. During desensitization treatment, 50 μl to 200 μl of an allergen-contaiping composition is administered directly into the lymph node starting with very small doses of allergen, from 0.1 μg up to 10 μg. This dose is one-tenth the normal dose for subcutaneous immunotherapy, and therefore the possibility of side effects is minimized.

The dose employed dinjng the maintenance phase can be from about 0.01 μg to about 10 μg or 0.1 μg to 50 μg, preferably 0.1 μg to 20 μg, delivered periodically over the course of from several months to several years. During maintenance treatment, the patient's lymph node is injected with from 0.1 μg to 50 μg of allergen in injections of typically 50 μl to 200 μl each. One skilled in the art will recognize that even smaller quantities of carrier are feasible.

Figure 1:
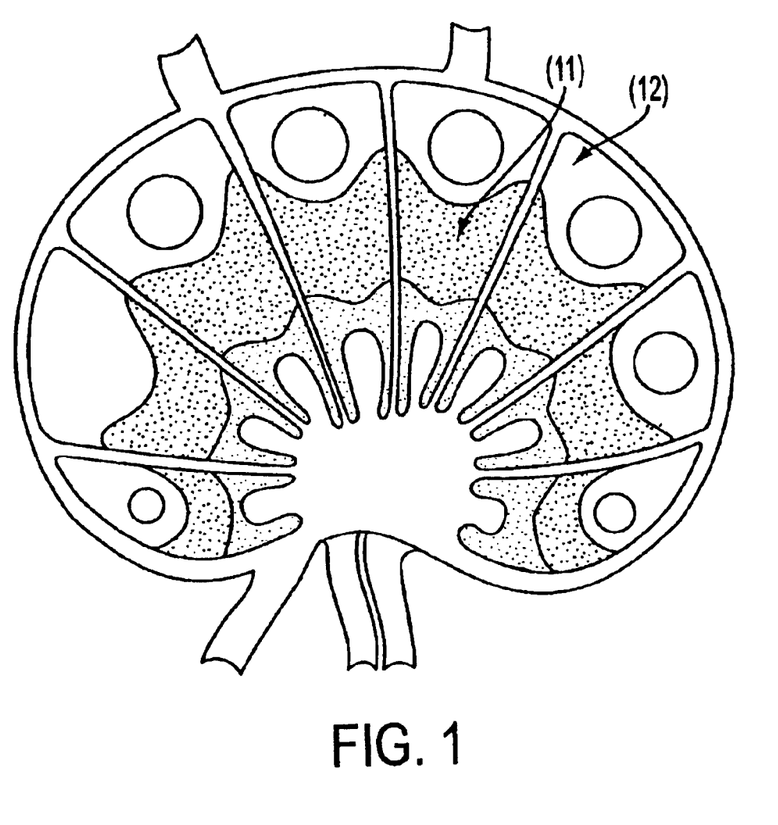
FIG. 1 is a diagram of a lymph node, with medullary (11) and cortical (12) areas shown.

Optionally, a lymph node may be visualized during the injection procedure. Ultrasound, radiological, or other visualization means such as computerized axial tomography (CAT scan), can be used to visualize the lymph node and monitor location of the needle and changes in the lymph node, such as swelling. Injection into the axillary and inguinal lymph nodes is preferred due to ease of ultrasound guided location and injection. FIG. 1 is a diagram of a lymph node, with arrows showing the medullary (11) and cortical (12) areas.

Figure 2:
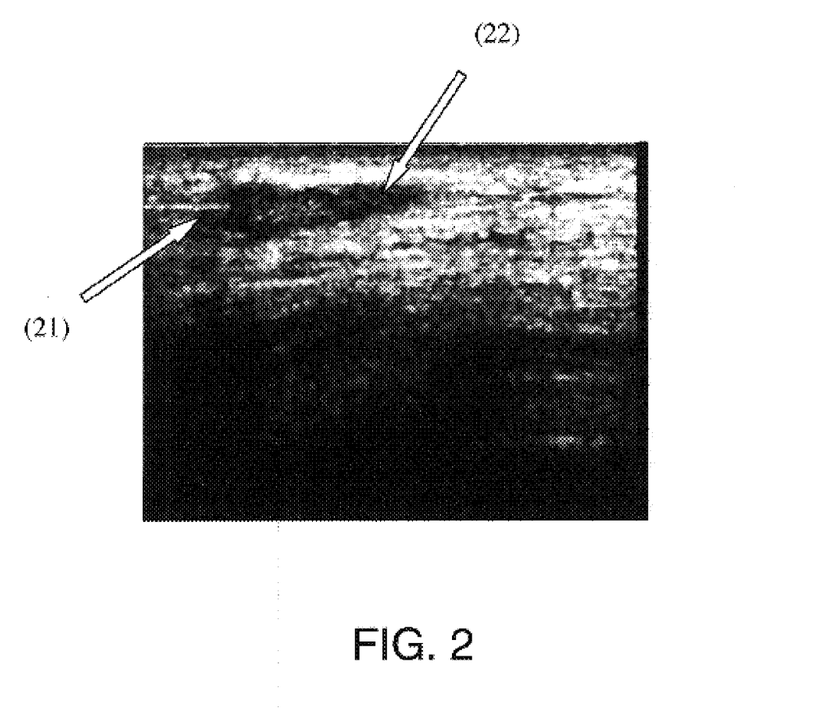
FIG. 2 shows an ultrasound image of a needle (21) inserted into an inguinal lymph node (22).
Figure 3:
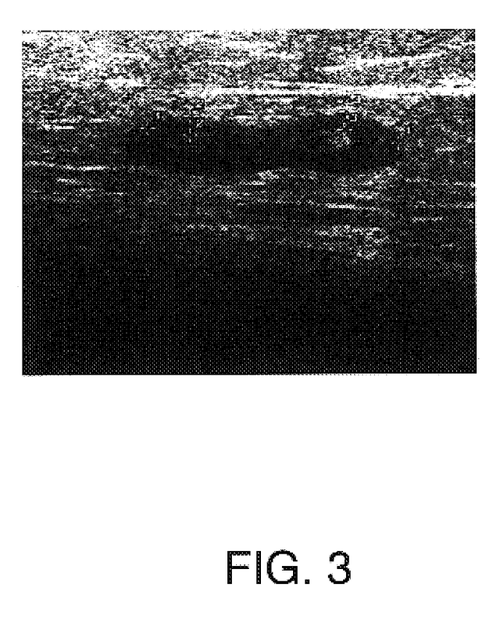
FIG. 3 shows an ultrasound image of an inguinal lymph node before intranodal vaccine delivery.
Figure 4:
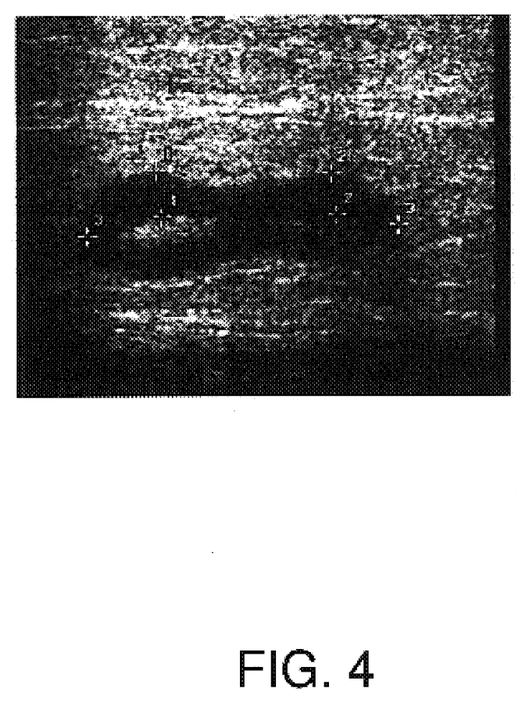
FIG. 4 shows an ultrasound image of an inguinal lymph node 6 days after intranodal vaccine delivery.

During administration of the allergen, the patient's vital signs typically are closely monitored, and the lymph node reaction is monitored, for example, by ultrasound or other visualization methods. FIG. 2 is an ultrasound image of a needle (21) inserted into an inguinal lymph node (22). FIG. 3 shows an ultrasound image of a lymph node taken before intranodal therapy. FIG. 4 shows an ultrasound image of the same lymph node after intranodal therapy.

The technique used for injection is within the skill of the art. One method is to use a dual-chamber syringe in which the allergen is included in one chamber and a liquid carrier in the other, to be mixed prior to injection.

In preferred embodiments of the invention, the allergen is delivered directly to the lymph node during both desensitization treatment and maintenance treatment. Alternatively, the allergen may be delivered directly to the lymph node during the desensitization phase and subcutaneously during the maintenance phase. Although less preferred, some of the benefits of the invention may be conferred if intranodal therapy is employed during desensitization and subcutaneous therapy is employed during maintenance.

To determine the efficacy of the allergen administration, the patient can be tested for baseline reactions before administration begins, using assays such as those for the measurement of IgG and IgE levels, T-cell stimulation, basophil activation, and/or controlled allergen exposures, such as skin tests and bee sting challenge. To determine whether a patient has been desensitized, one or more of these measurements can be compared to measurements taken after administration. Examples of suitable assays are provided in Example 14. It is well within the skill of the art to identify and employ alternative assays.

Efficacy of intranodal administration has been demonstrated in mouse models. In mouse models, intranodal therapy induces high IgG2a levels and no detectable IgE response, whereas conventional immunization induces high $T_H2$-dependent IgE levels and only low $T_H1$-dependent IgG2a levels. Stated otherwise, delivery of the intranodal formulations in minute and otherwise non-immunogenic concentrations induces strong $T_H1$ responses, leading to higher and longer lasting IgG2a responses than conventional immunotherapy.

The fact that intranodal administration of $PLA_2$ induces high IgG2a responses was shown when different amounts of $PLA_2$ were delivered in mice by direct injection into an inguinal lymph node and compared to conventional subcutaneous $PLA_2$ injections (FIG. 5). Blood was sampled for IgG2a antibody responses at 2, 4, 6, 8 and 10 weeks. In contrast to conventional results on IgG2a induction, low dose intranodal therapy with $PLA_2$ is sufficient to induce a strong IgG2a response, but only a weak IgE response (FIG. 6). With these low dose injections, no significant IgE titers were induced by either delivery.

The intranodal therapy, using approximately 1/1000 of the antigens required in the conventional formulation, induced IgG2a titers in five out of five mice with an average titer of 1:1000, whereas conventional therapy with the same dose induced no measurable IgG2a titers. A strong IgG2a response was induced in two out of three mice by intranodal injection of only 0.1 μg of $PLA_2$. In contrast, conventional treatment with the same dose induced no significant IgG2a response. To induce even a very low IgG2a response against $PLA_2$ using the conventional therapy, 10 μg of the allergen must be used for immunization.

Figure 7A:
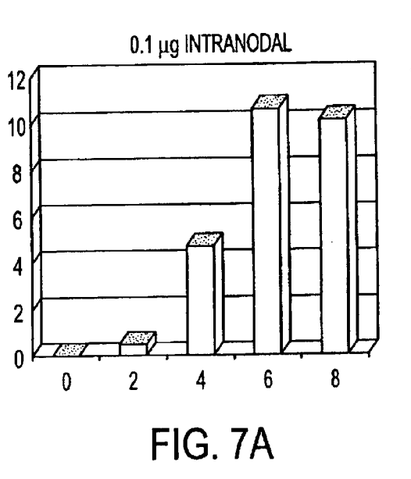
FIG. 7A, IgG2a levels detected by ELISA at 2, 4, 6 and 8 weeks after intranodal delivery of $PLA_2$.
Figure 7B:
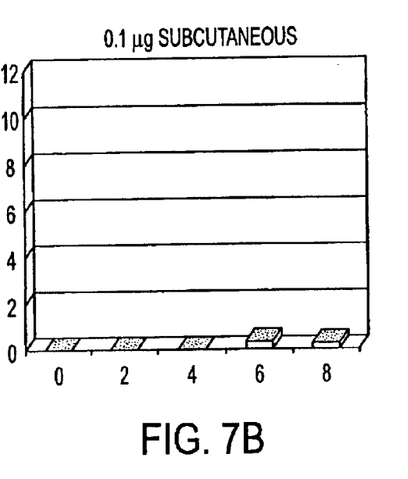
FIG. 7B, IgG2a levels 2, 4, 6 and 8 weeks following subcutaneous injection with $PLA_2$.
Figure 8A:
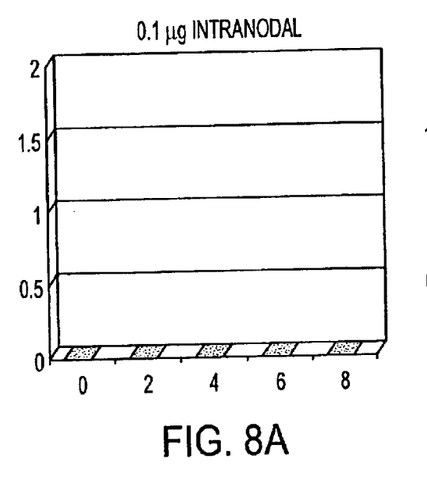
FIG. 8A shows that there is no IgE activity during the 8 weeks following intranodal delivery of $PLA_2$.
Figure 8B:
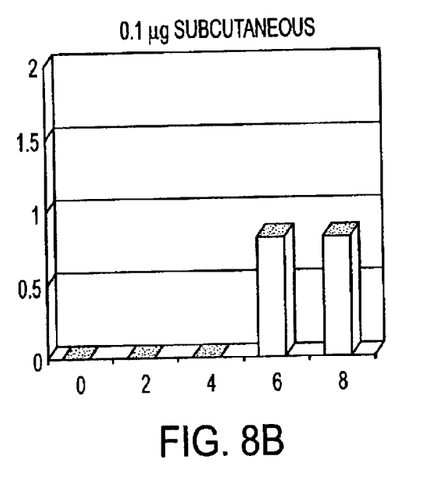
FIG. 8B shows the levels of IgE activity 6 weeks and 8 weeks following subcutaneous injection with $PLA_2$.

FIG. 7 shows the IgG2a response 2, 4, 6, and 8 weeks after intranodal and subcutaneous therapy. Injection of $PLA_2$ using intranodal delivery activates IgG2a at a dose (0.1 μg) that is ineffective with subcutaneous delivery. In FIG. 8, IgE activity levels after 2, 4, 6 and 8 weeks of therapy are shown. Injection of $PLA_2$ using intranodal delivery does not activate IgE production.

These results confirm the superiority, in form and extent, of the response from intranodal therapy. Titrations show that intranodal injection corresponds to increasing the conventional subcutaneous dose approximately 1000-fold, without increasing the side effects.

Allergens or compositions comprising allergens can be provided in a kit. The kit can contain a composition comprising an allergen and a physiologically acceptable carrier, as well as instructions for the methods described herein. The kit also can contain a syringe, such as a dual-chambered syringe. Optionally, the syringe can be prefilled with the allergen-containing composition. If prefilled, the syringe contains an appropriate dosage of the composition, typically not exceeding a concentration of 100 μg/ml.

The following examples demonstrate various allergen-containing preparations, different routes of administration with the exemplary allergen $PLA_2$, the major allergen of bee venom, and several means to measure the efficacy of this strategy. It is shown that direct delivery into the inguinal lymph node induces allergen-specific IgG2a titers more than 100 times more efficiently than intraperitoneal or subcutaneous injection. Among the IgG subclasses, IgG2a is known to be the most strictly $T_H1$-dependent subclass, thus indicating a strong $T_H1$ response against the allergen. Such a $T_H1$ response is desired, since it counteracts the $T_H2$ response, which is responsible for IgE production in allergic individuals. The examples are included for illustrative purposes only and are not intended to limit the scope of the invention, which is defined by the appended claims.

EXAMPLES

Example 1

Preparation of Bee Venom Allergen

Bees were collected and frozen immediately for storage. The insects were then thawed, and the venom sacs were dissected and placed in 5% sucrose solution (pH4.5–5.5). The sacs were washed a few times, then homogenized, and the insoluble debris was filtered out using a 0.22 μm membrane.

The protein concentration of the filtered venom solution was measured using a Coomassie dye binding assay and was diluted to the required concentration using a 5% sucrose solution. This was added with 0.01% Tween 80 and 0.01% Pluronic F68. The solution was sterile filtered through a 0.22 μm membrane, dispensed into vials, and lyophilized. After the lyophilization cycle, the vials were sealed under vacuum. Before administration, the vaccine was reconstituted using Water For Injection USP.

Example 2
Preparation of Yellow Jacket, Hornet or Wasp Venom Allergen

Yellow jackets, yellow hornets, or wasps are collected and frozen immediately for storage. The insects are then thawed and the venom sacs dissected and placed in 0.025M beta alanine/acetic acid buffer (pH 4.8) in 0.54% sodium chloride. The sacs are then homogenized and the insoluble debris separated by centrifugation. The supernatant containing the venom is filtered using a 0.22 μm membrane, mixed with bulking agents such as mannitol, dispensed into vials, and lyophilized. The vials are then sealed under vacuum. For administration, the vaccine is reconstituted using a pharmaceutically acceptable solution, such as normal saline, or 5% dextrose. Preparation of these vespid venoms may also be the same as for preparation of honeybee venom in Example 1 above.

Example 3
Preparation of Microencapsulated Bee Venom Vaccine

Bee venom protein (1 mg) is dissolved in 100 μl water or aqueous solution. PLGA, a biodegradable polymer (100 mg) is dissolved in 1 ml methylene chloride. The bee venom solution is added into the PLGA solution and homogenized, resulting in a water-in-oil emulsion. The water-in-oil emulsion is poured into 5% PVA aqueous solution (10 ml) and stirred to produce a water-in-oil-in-water emulsion. This emulsion is added to 100 ml 1% PVA solution to extract the methylene chloride. The microspheres are collected by centrifugation, washed 3 times with distilled water, and lyophilized.

Example 4
Purification of a Peptide Allergen Vaccine $PLA_2$ is a polypeptide (MW 19000) and is the major allergen in bee venom. It can be purified through reverse phase HPLC. Crude bee venom is dissolved in water at 10% concentration and filtered through a 0.22 μm membrane. The filtered bee venom solution (500 μl) is injected into a Brownlee Aquapore RP300 CB column equilibrated with 0.1% TFA running at 1 ml/min. The column is eluted with a gradient of acetonitrile from 0 to 60% over 45 minutes at 1 ml/min. One ml fractions are collected and analyzed using UV absorbance at 280 nm. The identity and purity of collected fractions are analyzed using SDS-PAGE. Pure $PLA_2$ fractions are pooled and lyophilized. $PLA_2$ fractions containing impurities are purified again using the reverse phase HPLC.

Example 5
Preparation of an Allergen Vaccine from a Purified Extract $PLA_2$, the major allergen component in bee venom, is purified using chromatography and can be purchased from commercial sources such as SIGMA. $PLA_2$ is dissolved in pharmaceutically acceptable injectable solution, such as water, normal saline, 5% dextrose water, or Ringer's solution. The $PLA_2$ solution is used in intralymphatic delivery.

Example 6
Preparation of an Allergen Vaccine from a Crude Extract

Honeybee venom can be collected from bee stings through electrostimulation. The bee venom can be air dried for storage. To prepare the vaccine, the honeybee venom is dissolved in 0.025M beta alanine/acetic acid buffer (pH 4.8) in 0.54% sodium chloride. Insoluble matter is removed using a 0.22 μm sterile filter. The pH of the solution is adjusted to neutral using phosphate buffer and the solution is used directly as bee venom vaccine. Alternatively, the bee venom solution can be lyophilized for storage stability.

Example 7
Preparation of an Allergen Vaccine from Transfected Cells

Human 293 HEK cells are transfected with pIND/V5-His (Invitrogen) containing a full-length cDNA clone of phospholipase $A_2$ ($PLA_2$) from honeybee. $PLA_2$ is engineered to contain a 6-histidine tag at its N-terminus. T-175 flasks containing approximately $5 \times 10^6$ cells are transfected with 15 μg plasmid using LipofectACE™ Reagent (GIBCO BRL). Forty-eight hours after induction, cells are harvested, dissolved in NP40 lysis buffer, and passed over a Ni column. Recombinant $PLA_2$ is eluted with 200 mM imidazole and the protein is analyzed by SDS-PAGE, protein staining, and western blot.

Example 8
Preparation of an Allergen Vaccine from a Mixture of Multiple Allergens Venom from various species of yellow hornets and wasps is dissolved in beta alanine/acetic acid buffer in the appropriate proportions. This solution is lyophilized in the presence of bulking agents such as mannitol and sucrose, and reconstituted before administration.

Example 9
Preparation of a Nucleic Acid Allergen Vaccine

Honeybee $PLA_2$ is amplified from MRNA prepared from fresh venom glands using RT-PCR and specific primers. The amplified product is then subcloned into pcDNA1.1/Amp (Invitrogen). Plasmids containing the insert are screened by restriction analysis, then sequenced in their entirety. Expression of $PLA_2$ is monitored as described in Example 6. Plasmid is amplified in *E. coli* DH5a cells and purified using the Qiagen plasmid purification system.

Example 10
Preparation of an Adjuvant Vaccine

Adjuvant vaccine can be prepared by adsorbing vaccine to an adjuvant or encapsulating the vaccine in a carrier material such as a polymer or lipid. The adsorption is performed simply by mixing vaccine with the adjuvant under appropriate conditions. For example, bee venom vaccine solution is added to an alum suspension at pH>5. Similarly, bee venom can be added to an oil-in-water emulsion, pluronic surfactant solution, or PLGA microsphere suspension to stimulate immunological response. The vaccine encapsulation is performed using various procedures such as spray drying, solvent evaporation, coacervation, precipitation, or blending. The process of encapsulating bee venom is described in Example 3.

Example 11
Use of Ultrasound to Locate Lymph Node

A lymph node is localized under ultrasound guidance. Inguinal lymph nodes have relatively low lymph flow and are located away from major blood vessels. Overview of the inguinal area is obtained to select a lymph node for delivery of vaccine. The lymph node with the greatest longitudinal axis (c. 1–1.5 cm) is selected to facilitate placement of needle. Ultrasound is used to guide the needle and to monitor the lymph node, ensuring that the allergen is delivered into the lymph node.

Example 12
Administration of an Allergen Vaccine to a Lymph Node

A lymph node is located under ultrasound guidance. The patient is shaved at the injection site. Wearing surgical gloves, the ultrasound operator disinfects the site. The ultrasound probe is covered with sterilized contact gel. The needle is introduced into the cortex of the lymph node, and the position of the tip is evaluated by moving it slightly and monitoring its position using the ultrasound machine. When the position appears correct, the vaccine is delivered directly into the lymph node, starting with very small doses. The dose is increased similarly to the standard protocol used for subcutaneous desensitization. All vital parameters of the patient are closely monitored and the lymph node reaction is monitored by ultrasound.

Subsequent ultrasound monitoring of the lymph node shows increased size of the paracortical area. Because this is the location in the lymph node of T lymphocytes, this increase in the diameter likely indicates specific T-cell activity, as opposed to swelling in the medullary area, which would suggest non-specific inflammation or edema. This enlargement diminishes by the end of treatment, apparently indicating that the lymph node retains not only its normal morphology but also its normal function.

Example 13
Schedule of Administration of Allergen

Three 100 ml injections containing from 0.1 µg to 10 µg of allergen each are administered 1 to 2 weeks apart, with possible subsequent maintenance injections or boosters of from 0.1 µg to 50 µg of allergen in 100 ml injections, delivered periodically for a period of from several weeks to several years.

Example 14
Assay for Efficacy of an Allergen Vaccine

To show that lymph node therapy results in modulation, diminution or elimination of allergic reaction, or lowered sensitivity to an allergen, correlative endpoints were reported which include measurement of IgG and IgE levels, changes in $T_H1/T_H2$ balance by cytokine or chemokine measurement, as well as changes in basophil activation. Alternatively, assays utilizing ELISPOT or RAST, and exposure tests such as skin tests or bee sting may be used to determine a change in reaction.

According to data from an ongoing pilot study, there was no substantial increase in allergen specific IgE levels in patients vaccinated with honeybee venom vaccine. Patients in this study received 3 treatments, 2 weeks apart. At the first treatment visit, patients were injected with 0.1 µg, 1 µg, 5 µg, and 5 µg. At treatments 2 and 3, patients received one 10 µg injection. In addition to IgE levels, total bee venom-specific IgG and IgG4 were measured pre-injection, 2 weeks later, and 4 weeks later. There was no significant increase in total bee venom specific IgG. However, the patients' IgG4 levels increased 50–160% above baseline following vaccination, which is similar to the increase seen in rush and ultrarush immunotherapy. This increase in IgG4 resulted in a change in the individual's IgG ratio. Within this embodiment, systemic mast cell degranulation does not occur, as would be evidenced by an increase in serum tryptase.

A. Induction of an IgG Response

Two doses of the bee venom allergen $PLA_2$ were injected into a mouse, and the IgG2a titer was quantitated over time. The $PLA_2$ was injected with the adjuvant alum. Three different delivery sites were chosen: into a lymph node, subcutaneous, and intraperitoneal.

Figure 5A:
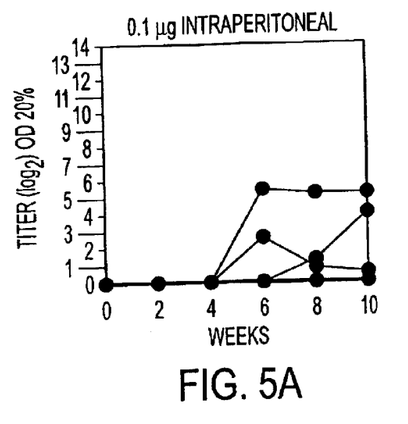
Figure 5B:
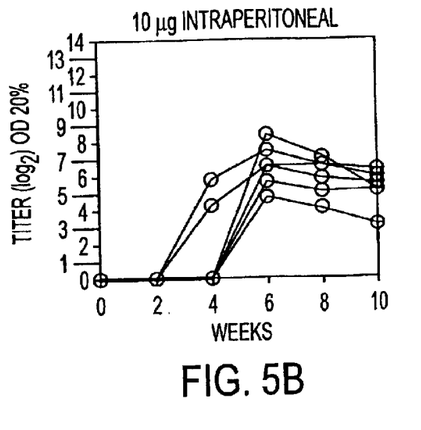
Figure 5C:
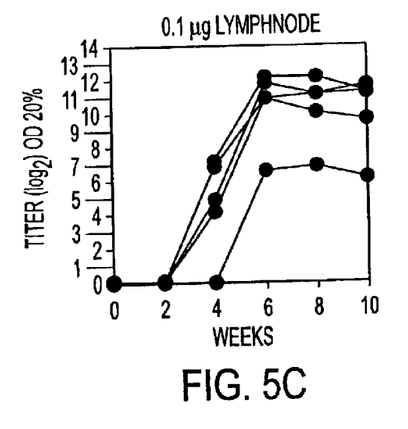
Figure 5D:
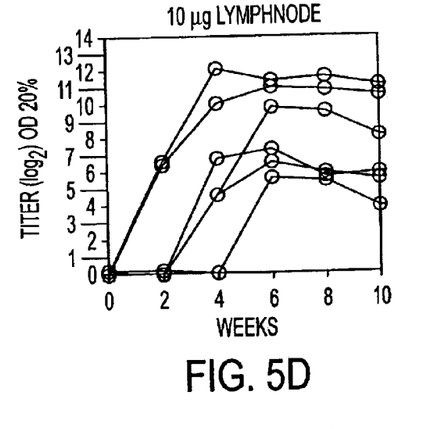
Figure 5E:
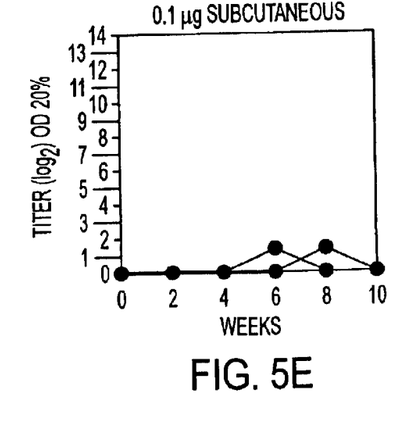

Injection with 0.1 µg of $PLA_2$ into the inguinal lymph node induced IgG2a titers in 5 out of 5 mice, with an average titer of approx. 1:1000 (FIG. 5C). This response was not enhanced with increased dosage (FIG. 5D). Injection of the same dose subcutaneously induced no measurable IgG2a titers (FIG. 5E). Injection of 0.1 µg intraperitoneally induced low IgG2a titers (approx. 1:16) in only 2 out of 5 mice (FIG. 5A).

Figure 5F:
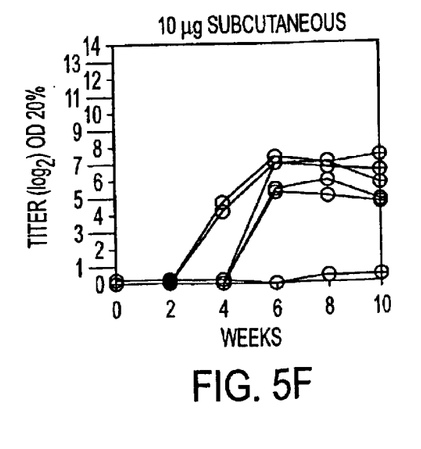
Figure 6A:
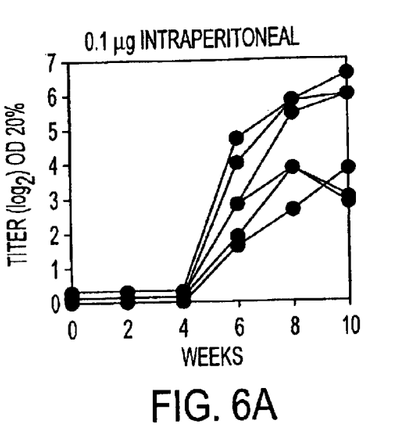
Figure 6B:
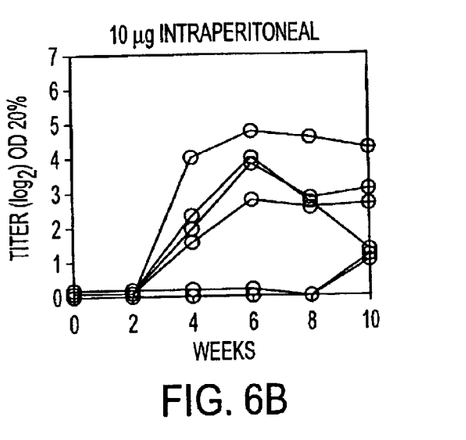
Figure 6C:
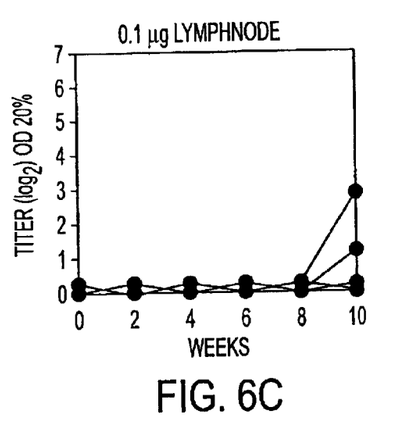
Figure 6D:
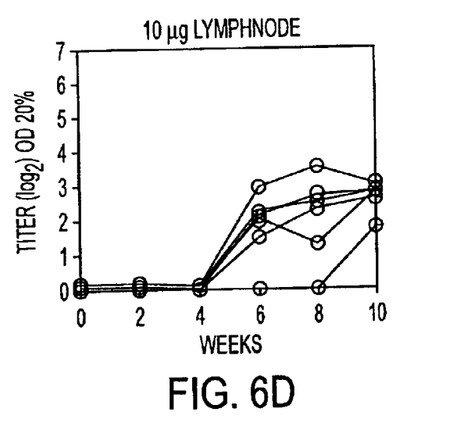
Figure 6E:
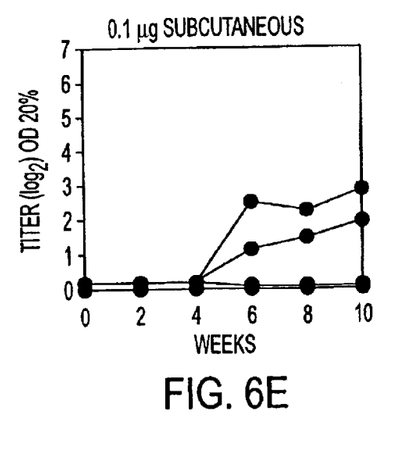
Figure 6F:
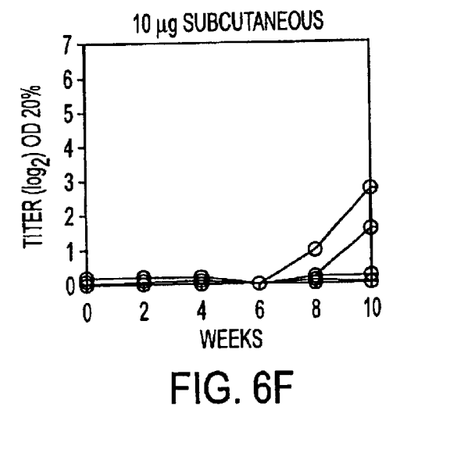

To induce specific IgG2a against $PLA_2$ via the intraperitoneal or the subcutaneous route, 10 µg of the allergen were required (FIG. 5B+F). However, the induced titers were only approximately 1:50 (FIG. 5B+F) and were thus only at a level of 5% of the titers induced by the lower dose of $PLA_2$ injected intranodally (FIG. 5C).

Thus, intranodal delivery induced allergen-specific IgG2a antibody responses that are 20 times higher using only 1% of the allergen dose. Because side effects are directly proportional to the allergen dose, intranodal vaccination with allergens not only desensitizes more efficiently, but also likely produces fewer side effects.

B. Diminished IgE Response

Two doses of the bee venom allergen $PLA_2$ were injected into a mouse, and the IgE titer was quantitated over time. The $PLA_2$ was injected with the adjuvant alum. Three different injection sites were chosen: into a lymph node, subcutaneous, and intraperitoneal.

Intranodal injection of the allergen $PLA_2$, although it induced IgG titers more efficiently, did not induce IgE titers more efficiently. Injection into a lymph node with $PLA_2$ induced less IgE than intraperitoneal or subcutaneous injection (FIG. 6).

C. In Vitro Stimulation of Patient T Cells with Bee Venom Antigen

CD4 T-cell responses to the allergen are assayed in patients treated with intralymphatic bee venom. Before and after injection, whole blood is drawn and PBMC is isolated by ficoll-hypaque density gradient sedimentation. One million PBMC are placed in 12×75 mm polystyrene tissue culture tubes containing 2 ml complete medium. PBMCs are cultured with bee venom, PHA, or negative controls for 6 hours with the final 5 hours including 10 µg/ml Brefeldin A (Sigma). After incubation, cells are harvested by washing once in ice cold PBS, resuspended in PBS with 0.02% EDTA, incubated at 37° C. for 15 minutes, and washed once more in ice cold PBS. Cells are harvested by resuspension in either PBS for immediate analysis or in 4% paraformaldehyde in PBS for later use. Cells are then frozen for intracellular cytokine staining.

Assays may also be performed directly on whole blood, using a whole blood activation system, such as Becton Dickinson's FastImmune Cytokine System, to detect cytokine activity.

D. Analysis of CD4 T-Cell Cytokine Production by Flow Cytometry

Frozen cells are rapidly thawed to 37° C. and then washed once in ice cold PBS/0.1% Na azide/1% FCS before resuspension in fixation/permeabilization solution. The cells are fixed and permeabilized for 10 minutes. Intracellular cytokines are detected by incubation with anti-cytokine antibodies (IL-2, IL-4, IL-5, IL-13, IFN-γ, and TNF-α) for 30 minutes. Cells are blocked with anti-FC receptor for 3 minutes, then washed. Surface markers are detected by incubation with anti-CD4, anti-CD8 and anti-CD69 for 20 minutes on ice. Cells are then washed again. Fixed and permeabilized cells are incubated on ice with directly labeled Mab to CD4, IFN-γ, IL-2, and CD69 or CD4, IL-4, IL-5 and CD69 for 30 minutes, then are washed and resuspended in 1% paraformaldehyde. In addition, the number of cells stained with $T_H1$ cytokines and $T_H2$ cytokines are compared directly with one another, for example IFN-γ and IL-4 with CD4 and CD69. Flow cytometry is performed with a FACScan using 4 channels with FITC, PE, PerCP, or AP as fluorochromes. All analyses include a minimum assessment of CD4+, CD69+ vs. cytokine, or isotype matched controls, to search for cytokines from activated T cells (IL-2, IL-4, IL-5, IL-13, IFN-γ, and TNF-α). For each analysis 50,000 events are acquired and gated on CD4 expression. In addition, a gate is used to include only viable small lymphocytes by forward and side scatter. CellQuest is used for data analysis.

E. Analysis of Basophil Response by Flow Cytometry

Whole blood is stimulated with allergen, stained by FACS, and gated on a CD123+, HLA-DR population with low side scatter (basophils). Detection is by CD63 (an alpha granule antigen). Expression of CD63 increases in allergic individuals following stimulation with antigen.

F. IFN-γ ELISPOT

Ninety-six-well HA plates are coated with 100 µl anti-IFN-γ (5 µg/ml in ELISA coating buffer, pH 9.6, filter sterilized) and incubated at 4° C. overnight. Plates are washed 4 times in sterile PBS, then blocked with 200 µl/well RPMI 1640/10% FCS/2% penicillin (v/v/v) streptomycin, glutamine, for at least 2 hours at room temperature. Blocking solution is discarded and plates are washed 3 times with sterile PBS. Cells are added at $5 \times 10^5$/well in 100 µl and 4 doubling dilutions are made. Control wells contain no cells.

Plates are incubated at 37° C./5% $CO_2$ for 20 hours. Plates are washed 3 times in PBS, then 3 times in wash buffer. Polyclonal rabbit-α-mouse IFN-γ (100:1 $\frac{1}{1000}$ (v/v) dilution in RPMI/10% FCS/2% PSG) is added, and plates are incubated overnight at 4° C. Plates are washed 3 times in PBS. An α-rabbit IgG alkaline phosphatase conjugate (Sigma) is added at a dilution of $\frac{1}{20,000}$ (v/v) in 100 µl PBS/0.05% Tween (v/v) containing 1% (w/v) BSA (BDH). Plates are incubated overnight at 4° C.

Plates are washed 4 times with PBS. Spots are developed by incubation with 5-bromo-4-chloro-3-indolyl phosphate (BCIP/NBT Sigma Fast Tables Sigma)(1 tablet in 10 ml distilled water) for 30 minutes at 37° C. Plates are washed with water and air dried for 2 hours. Spots are counted using a dissecting microscope.

Quantification of Cytokine-Producing Cells by ELISPOT

Ninety-six-well HA plates are coated with anti-cytokine antibody and incubated at 4° C. overnight. Plates are washed 4 times in sterile PBS and blocked to minimize nonspecific binding. Blocking solution is discarded and plates are washed 3 times with sterile PBS. Cells are added at $5 \times 10^5$/well in 100 µl, and 4 doubling dilutions are made. Control wells contain no cells.

Plates are incubated at 37° C./5% $CO_2$ for 20 hours. Plates are washed 3 times in PBS, then 3 times in wash buffer. Anti-cytokine secondary antibody is added and plates are incubated overnight at 4° C. Plates are then washed 3 times in PBS. An alkaline phosphatase-conjugated antibody which recognizes the secondary antibody is added in 100 µl PBS/0.05% Tween (v/v) containing 1% (w/v) BSA, and plates are incubated overnight at 4° C.

Plates are washed 4 times with PBS. Spots are developed by incubation with 5-bromo-4-chloro-3-indolyl phosphate (BCIP/NBT Sigma Fast Tablets, Sigma) (1 tablet in 10 ml distilled water) for 30 minutes at 37° C. Plates are washed with water and air dried for 2 hours, after which spots are counted.

G. RAST

Radio-Allergosorbent Test is a blood test used to monitor response to immunotherapy. Blood is collected from a vein, finger, heel, or earlobe, transferred to sterile tubes, and treated with anticoagulant. Whole blood is then measured by radioimmunoassay for IgE antibodies, detection of which would indicate allergic response. Detection of no IgE levels indicates absence of hypersensitivity.

H. Skin Test

Skin testing may be performed by prick or by intradermal methods. Prick-puncture is performed by placing a drop of allergen and a drop of control solution 2 cm apart on the arm. A disposable hypodermic needle is passed through the drop and into the skin surface. The needle tip is lifted up, elevating the epidermis without causing bleeding, then withdrawn, and the solution wiped away after 1 minute. Intradermal tests are performed by injecting approximately 0.01 to 0.05 ml of the allergen into the superficial layers of the skin, avoiding the subepidermal capillary bed. This should produce a small bubble approximately 2 to 3 mm in diameter. A 3 mm wheal accompanied by 10 mm flare and itching are likely to represent a positive immunologic reaction and to indicate presence of IgE antibodies.

I. Bee Sting Challenge

A bee sting challenge is performed by application of a live honeybee to the patient's forearm, allowing it to sting the patient. This is a standard general test for efficacy known in the art. This challenge only produces a minimum local reaction in a patient who has been desensitized.

What is claimed is:

1. A method of desensitizing a human to an allergen against which the individual mounts an allergic response, wherein the allergen is selected from the group consisting of venom, animal dander, pollen, and dust mite comprising the step of delivering the allergen directly into a lymph node of the human, wherein no more than three injections of 1 ug once per month of the allergen are sufficient to desensitize the human to the allergen as assessed by sensitivity of the human to the allergen.

2. The method of claim 1 wherein said lymph node is an axillary lymph node.

3. The method of claim 1 wherein said lymph node is an inguinal lymph node.

4. The method of claim 1 wherein the allergen is delivered to an antigen presenting cell within the lymph node.

5. The method of claim 1 wherein the allergen is delivered to an immune cell within the lymph node.

6. The method of claim 1, further comprising the step of using an ultrasound device to monitor location of an injection needle.

7. The method of claim 1, further comprising the step of visualizing the lymph node using a radiological method.

8. The method of claim 1 wherein the allergen is an extract or a purified substance.

9. The method of claim 1 wherein the allergen is selected from the group consisting of a recombinant protein and a synthesized peptide.

10. The method of claim 1 wherein the allergen is accompanied by a physiologically acceptable carrier.

11. The method of claim 1 wherein the allergen is accompanied by an adjuvant.

12. The method of claim 1 wherein the step of delivering is carried out at least twice.

13. The method of claim 1 wherein the allergen is delivered into the lymph node with a syringe.

14. The method of claim 13 wherein the syringe is a dual-chambered syringe.

15. The method of claim 1 wherein the allergen is pollen.

16. The method of claim 1 wherein the allergen is venom.

* * * * *

UNITED STATES PATENT AND TRADEMARK OFFICE
CERTIFICATE OF CORRECTION

PATENT NO. : 6,773,695 B2 Page 1 of 1
APPLICATION NO. : 09/804464
DATED : August 10, 2004
INVENTOR(S) : Thomas M. Kündig et al.

It is certified that error appears in the above-identified patent and that said Letters Patent is hereby corrected as shown below:

On the Title Page, Assignee section (73):
  Please insert --University of Zürich, Zürich, Switzerland--

Signed and Sealed this

Twenty-ninth Day of April, 2008

JON W. DUDAS
*Director of the United States Patent and Trademark Office*